United States Patent
Suckewer et al.

(10) Patent No.: US 8,382,744 B2
(45) Date of Patent: Feb. 26, 2013

(54) METHOD AND DEVICE FOR CORNEA RESHAPING BY INTRASTROMAL TISSUE REMOVAL

(76) Inventors: Szymon Suckewer, Princeton, NJ (US);
Peter Hersh, Far Hills, NJ (US);
Alexander Smits, Princeton, NJ (US);
Anatoli Morozov, Hightstown, NJ (US)

(*) Notice: Subject to any disclaimer, the term of this patent is extended or adjusted under 35 U.S.C. 154(b) by 1523 days.

(21) Appl. No.: 11/843,498

(22) Filed: Aug. 22, 2007

(65) Prior Publication Data

US 2008/0051772 A1   Feb. 28, 2008

Related U.S. Application Data

(60) Provisional application No. 60/839,460, filed on Aug. 23, 2006.

(51) Int. Cl.
*A61F 9/007* (2006.01)
(52) U.S. Cl. .............................. 606/5; 128/898
(58) Field of Classification Search .................. 128/898; 606/4–5
See application file for complete search history.

(56) References Cited

U.S. PATENT DOCUMENTS

| | | | | |
|---|---|---|---|---|
| 5,722,971 A | * | 3/1998 | Peyman | 606/5 |
| 6,110,166 A | * | 8/2000 | Juhasz | 606/5 |
| 2003/0014042 A1 | * | 1/2003 | Juhasz et al. | 606/5 |
| 2004/0243111 A1 | * | 12/2004 | Bendett et al. | 606/5 |
| 2007/0219542 A1 | * | 9/2007 | Yahagi | 606/5 |
| 2008/0039825 A1 | * | 2/2008 | Lai | 606/5 |
| 2008/0071258 A1 | * | 3/2008 | Lemberg et al. | 606/33 |
| 2008/0147052 A1 | * | 6/2008 | Bendett et al. | 606/5 |
| 2009/0012506 A1 | * | 1/2009 | Feingold | 606/5 |

* cited by examiner

*Primary Examiner* — Henry M Johnson, III
(74) *Attorney, Agent, or Firm* — Roy Rosser

(57) ABSTRACT

A method and device for flapless, intrastromal keratomileusis for the correction of myopia, hyperopia and astigmatism, i.e., for vision correction by corneal reshaping without creating a flap. Ultra-short laser pulses are used to create a temporary micro-channel extending to an end point located within the cornea. A second series of ultra-short laser pulses are then delivered to photo-ablate material in the vicinity of the micro-channel end-point. The photo-ablated material may exit through the micro-channel used to deliver the laser pulses, or via a separate micro-channel. With the micro-channel oriented substantially normal to the optical axis of the cornea, and by continuing to supply the ultra-short laser pulses in the appropriate number while moving the point of ablation along the micro-channel, the photo-ablation of the intrastromal tissue may continue in a controlled fashion and the cornea reshaped in a predetermined manner without creating a flap.

4 Claims, 9 Drawing Sheets

METHOD AND DEVICE FOR CORNEA RESHAPING BY INTRASTROMAL TISSUE REMOVAL

CROSS REFERENCE TO RELATED APPLICATIONS

This application is related to, and claims priority from, U.S. Provisional Patent application No. 60/839,460 filed on Aug. 23, 2006, by Suckewer et al. entitled "Method and Device for Corneal Reshaping without creating a Flap", the contents of which are hereby incorporated by reference.

FIELD OF THE INVENTION

The present invention relates to the correction of vision by reshaping the cornea, and more particularly to using a femtosecond laser for flapless, intrastromal keratomileusis for the correction of myopia, hyperopia and astigmatism.

BACKGROUND OF THE INVENTION

Laser-Assisted in Situ Keratomileusis (LASIK) is a well-known laser eye surgery for correcting defects of vision including myopia (commonly referred to as "short-sighted"), hyperopia (commonly referred to as "far-sighted"), and astigmatism.

LASIK is performed by first forming a thin hinged flap out of the top of the cornea. The hinged flap is then folded back and the shape of the exposed cornea is changed by using an excimer laser to ablate away material. After ablating away the required material, the flap is folded back into place. The flap typically heals back into place in a few days.

The thin flap may be formed by cutting with a microkeratome or by using a femtosecond laser to photodisrupt a thin layer of the cornea, as described in more detail below.

Reshaping of the cornea is a particularly effective way of correcting vision defects as, in the typical human eye, the refractive power of the cornea accounts for approximately two-thirds of the total refractive power of the eye. In addition, the procedure takes about fifteen minutes. Because of the speed, efficacy and simplicity, LASIK has become a very popular procedure, with over 24.6 million procedures already performed, and over 6 million procedures being performed annually at a cost of over $1000.00 per procedure.

Forming the flap remains the least predictable part of the LASIK procedure and currently limits the degree to which procedures can be customized for individual correction of vision defects. Moreover, imperfect healing of the flap is a factor in about 5% of the procedures and may lead to a variety of problems including, but not limited to flap striae, epithelial ingrowths beneath the flap, diffuse lamellar keratitis, and flap tears.

A highly desirable improvement to the important field of the correction of vision by reshaping the cornea would, therefore, be to eliminate the need for creating the flap in LASIK type procedures.

SUMMARY OF THE INVENTION

Briefly described, the invention provides a method and device for flapless, intrastromal keratomileusis for the correction of myopia, hyperopia and astigmatism, i.e., for the correction of vision by reshaping the cornea without the need to create a flap.

In a preferred embodiment of the present invention, a series of ultra-short pulses, such as those from Titanium-Sapphire femto-second laser, are used to create a temporary micro-channel extending from a surface of the cornea to a micro-channel end point located within the cornea. A second series of ultra-short laser pulses are then delivered in either a longer window of time, at a higher repetition rate, or at a higher pulse energy, or some combination thereof. This second series of ultra-short laser pulses results in the photo-ablation of material in the vicinity of the micro-channel end-point. The amount of material ablated in the vicinity of the micro-channel end point is typically proportional to the number of ultrashort laser pulses delivered to that point. The number of ultrashort laser pulses may, for instance, be controlled by controlling the length of the window of time in which the pulses are delivered, the repetition rate of the laser or the pulse energy of the individual ultrashort laser pulses, or some combination thereof. The photo-ablated material may be removed from the cornea through the same temporary micro-channel used to deliver the ultra-short pulses, or via a separate temporary micro-channel.

By having the temporary micro-channel oriented substantially normal, i.e., perpendicular, to the optical axis of the cornea, and by continuing to supply the ultra-short laser pulses in the appropriate number while moving the point of ablation along the micro-channel, the photo-ablation of the intrastromal tissue of the cornea may continue in a controlled fashion so that the cornea may be reshaped in a predetermined manner without the need to create a flap.

The procedure may be speeded up by simultaneously using two or more beams of laser pulses to create two or more temporary micro-channels through which the intrastromal photo-ablation can be directed.

The ultra-short laser pulses used in a preferred embodiment typically each have a temporal duration that is equal to or less than 20 picoseconds, a pulse energy that is equal to or less than 20 mJ and a repetition rate is equal to or greater than 100 Hertz, though they may have a temporal duration that is less than 500 femtoseconds, a pulse energy that is less than 2 mJ and may even have a temporal duration that is less than 50 femtoseconds, a pulse energy less than 500 µJ and be delivered at a laser repetition rate that is greater than 1 kilo-Hertz.

These and other features of the invention will be more fully understood by references to the following drawings.

DETAILED DESCRIPTION

Figure 1:
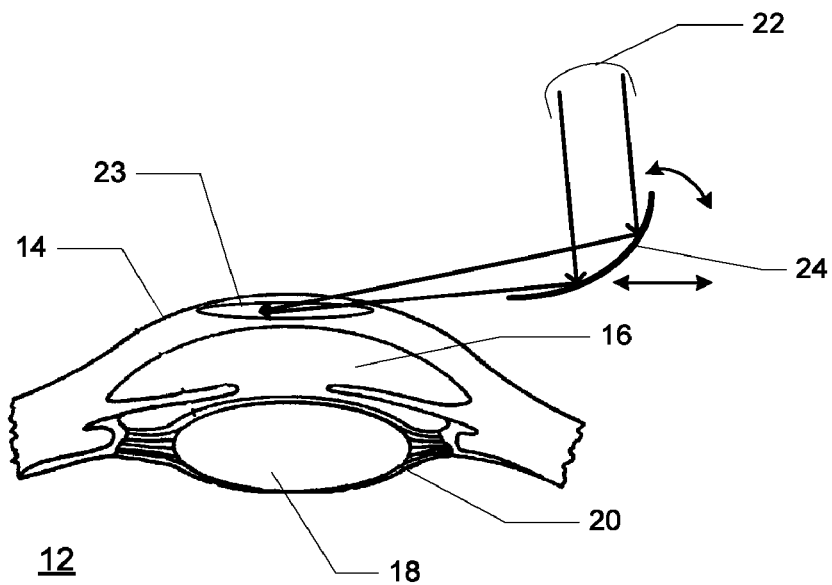
FIG. 1 is a schematic representation of one ultrashort laser beam focused at a point in the stroma bed of the cornea of the patient's eye.

The present invention relates to methods and devices that use a femto-second laser to perform intrastromal keratomileusis for the correction of myopia, hyperopia and astigmatism.

In a preferred embodiment, the laser beam is directed almost perpendicular (normal) to the optical axis of the eye being treated, i.e., the axis of the cornea. This is marked contrast to, for instance, the use of a femto-second laser for flap creation as marketed by, for instance, Intralase, Inc. of Irvine, Calif., in which the fsec laser beam is nearly parallel to the optical axis.

In the method of cornea reshaping of the present invention, the femto-second laser pulses are first used to create a temporary micro-channel. This micro-channel is used to deliver laser beam energy at the end of the channels to ablate cornea tissue. The intensity of the pulses that are used to ablate the intrastromal tissue are several orders of magnitude higher than the intensity of the pulses used for photo-disruption in the Intralase flap creation. In addition to delivering the laser pulses, the micro-channel may also be used to evacuate the gaseous, or liquid, ablated tissue. Alternatively, multiple laser beams may be used to create multiple temporary micro-channels, some of which may deliver laser pulses and some of which may evacuate ablated material. The additional, temporary micro-channels may directed to the ablation area from the same side of cornea or from the opposite side.

The method of the present invention may be use to remove an optical lenticule or disk of any reasonable shape. In a preferred embodiment, the amount of material ablated in the vicinity of the current end of the micro-channel is proportional to the number of laser shots pulses delivered to that point. In further embodiments of the invention, the number of shots to a given area may be varied by changing the window of time over which they pulses are delivered, the laser repetition rates, or the pulse energies. The number of laser shots to each area to be ablated may be controlled by computer, which may also provide a tracking guide, similarly to the present LASIK system, so that an optical lenticule of any shape including complex optical shapes may be removed.

In a preferred embodiment of the invention, the patient lies down under the laser. The patient's eye may then be coupled to the laser via a suction device and centration verified. The laser may then be used to make one or more temporary microchannels that may be used for laser pulse delivery and/or evacuation of ablated material. The laser pulses may then be delivered by, for instance, spinning mirrors that may be guided by input data in the form of, for instance spherocylindrical correction data or wavefront data. The ablated material may, for instance, be vented around the coupling device to the atmosphere. The procedure of this invention typically takes about 45-90 seconds.

Some of the technical details of the application are related to the PCT application entitled "Devices, Methods and Compositions for Presbyopia Correction Using Ultrashort Pulse Lasers" filed by on Mar. 5, 2007 as PCT application no. PRINCE-14206 by S. Suckewer et al., the contents of which are hereby incorporated by reference.

The present invention may be understood in relationship to several other new laser eye procedures that concern photoablation of eye tissue and that also relate to laser procedures such as LASIK.

For instance, U.S. Pat. No. 4,538,608, issued to L'Esperance, Jr. for "Method and Apparatus for Removing Cataractous Lens Tissue by Laser Radiation", the contents of which are hereby incorporated by reference, teaches how to deliver laser energy into the anterior of the eye lens and scan the laser beam in order to photoablate cataractous tissue, has general importance for the process of photoablation of eye tissue, including photoablation of stroma. This procedure was improved by J. Bille in U.S. Pat. No. 5,246,435 "Method for Removing Cataractous Material", the contents of which are hereby incorporated by reference and who teaches a procedure of laser energy delivery to separate lamellae in the stroma by focusing a laser beam between lamellae layers and photoablating tissue at the interface between these layers.

In these disclosures, nanosecond (nsec) type laser beams were considered (for example, 10-20 nsec excimer lasers, or 5-10 nsec Nd/YAG lasers, where 1 nsec=$10^{-9}$ sec). With these pulse durations, each laser shot, in addition to ablating tissue, creates strong shock waves within the eye and generates significant tissue heating. These effects are undesirable, and may be reduced by using lasers with shorter pulse durations. Therefore, when compact ultrashort lasers (with pulse durations less than 1 psec, where 1 psec=$10^{-12}$ sec) were developed in the late 1980's, they were immediately considered for use in eye surgery.

In a review article by Christopher Yo et al. on "LASIK, Future Advances" published in E-Medicine, Nov. 25, 2004, which is hereby incorporated by reference, the authors stressed (page 5) that " . . . one can assume the culprit that negates all the advantages of custom ablation may lie in the flap procedure itself. Hence, it would be a great leap in refractive surgery if the LASIK procedure can one day be completed intrastromally without the need for cutting a flap." In addition, the LASIK flap may lead to complications such as flap striae, epithelial ingrowths beneath the flap, diffuse lamellar keratitis, and flap tears.

Our invention of reshaping the cornea by means of using femtosecond-type of laser for correcting the refractive errors of myopia, hyperopia, and astigmatism without cutting a flap provides this desired corneal refractive surgery without a flap.

The general advantage of using fsec lasers for eye surgery compared to using much longer pulse lasers (nsec-type excimer, Nd/YAG or Nd/Glass lasers) is that with fsec lasers there is a much lower energy requirement, in particular when the surgery requires eye tissue ablation (that is, photo-ablation). The process of photo-ablation requires a certain intensity of laser beam. For the same ablated spot size, the intensity required for photo-ablation is inversely proportional to the pulse duration. For example, laser pulses of 100 fsec duration can cause photo-ablation, or tissue cutting, at hundreds of times smaller beam energies than when laser pulses of 10 nsec duration are used. This observation leads to three principal and important advantages of using ultrashort laser pulses for eye surgery. One advantage is that it is possible to perform much higher precision tissue cuts with such lasers when compared with nanosecond-type lasers. A second advantage is that ultrashort laser pulses produce much smaller heating effects in tissue when compared with longer laser pulses. A third advantage is that ultrashort laser pulses produce only very weak shock waves in tissue, whereas long laser pulses produce very substantial shock waves that can produce considerable trauma. In eye surgery, this trauma can have substantial negative effects on the prognosis following surgery, such as inflammation and complications in wound healing.

An explanation of these phenomena is offered by, for instance, G. Mourou et al. in U.S. Pat. No. 5,656,186 issued on Aug. 12, 1997 and entitled "Method for controlling configuration of laser induced breakdown and ablation", the contents of which are hereby incorporated by reference. Mourou teaches the relationship between laser fluence threshold for breakdown, and photo-ablation, in tissue and laser pulse duration. Fluence (symbol F) is the term used in photochemistry to specify the energy delivered in a given time interval, for instance by a laser pulse, and it is usually measured as the number of Joules deposited per square cm over a certain period of time ($J/cm^2$). Pulse duration is given the symbol $\tau$, and is usually measured in psec. It is shown by Mourou et al. that, starting at a fluence level of $F \approx 10$ $J/cm^2$ at a pulse duration $\tau \approx 10$ nanosecond (nsec), required fluence level (fluence threshold) decreases as $\tau^{1/2}$ over the range 10 nsec down to 10 picosecond, then decreases by a factor of two for pulse durations from 10 psec down to 1 psec, and then stays constant at $F \approx 0.4$ $J/cm^2$ down to 100 fsec. Therefore, for a pulse duration of $\tau \approx 10$ nsec, the typical energy (E) required to ablate a surface area of diameter $D \approx 100$ micrometer ($\mu m$) is $E \approx 1$ mJ, whereas with a pulse duration of $\tau \approx 100$-200 fsec (for such short pulses a typical $D \approx 20$ $\mu m$) the typical energy required is only $E \approx 1.6$ $\mu J$. Hence, to photoablate tissue using fsec rather than nsec laser pulses, the energy levels are more than 500 times smaller, and it is obvious that shock waves are negligibly weak for ultrashort pulse laser photoablation.

In addition to photoablation, laser pulses can be used to produce photodisruption. The photodisruption process results in the formation of bubbles (cavity bubbles, gas bubbles, and the associated shock waves) in the tissue, and it requires less intensity (less energy per pulse) than photoablation. Photodisruption is, therefore, also preferably conducted with fsec pulses, as indicated by T. Juhasz et al. in an article in the IEEE Journal of Selected Topics in Quantum Electronics 5, 902-909 (1999), the contents of which are hereby incorporated by reference. In conventional LASIK procedures where a flap is created by using a mechanical microkeratome, photodisruption provides the basis for replacing the mechanical flap cut by a much more precise flap cut using a fsec laser as detailed in, for instance, Juhasz et al.'s U.S. Pat. No. 5,993,438 that issued on Nov. 30, 1999 entitled "Intrastromal photorefractive keratectomy", T. Juhasz's U.S. Pat. No. 6,110,116 that issued on Aug. 29, 2000 entitled "Method for corneal laser surgery", and T. Juhasz et al.'s U.S. Pat. No. 6,146,375 that issued on Nov. 14, 2000 entitled "Device and method for internal surface sclerostomy," the contents of all of which are hereby incorporated by reference. U.S. Pat. No. 6,146,375 also teaches about using fsec or picosecond (psec) pulses for the treatment of glaucoma. T. Juhasz et al.'s research has led to the successful company Intralase, Inc. of Irvine, Calif., that markets the procedure for cutting the flap with a fsec laser in preparation for LASIK eye surgery, where the corneal correction itself uses an excimer laser providing pulses of 10-20 nsec duration.

Proposals to extend T. Juhasz et al.'s research and the IntraLase Company's experience with fsec lasers to the possibility of reshaping the cornea without first creating a flap are described in, for instance, K. Koenig's US Patent Application 2004/0102765 that was published on May 27, 2004 entitled "Method for minimal to non-invasive optical treatment of tissue of eye and for diagnosis thereof and device for carrying out said method," the contents of which are hereby incorporated by reference. The description in this application includes a proposed fsec laser setup for reshaping cornea without cutting the flap that appears to be similar to that by IntraLase for cutting the flap. The application appears to propose using fsec pulses that have nanoJoule energy per pulse. That is a much lower energy level per pulse than typically used in the IntraLase system, but at much higher repetition rate than typically used in that system. The laser beam appears to be operated nearly perpendicular to the surface of the eye, i.e., nearly parallel to the axis of the eye. Another such proposal is described in, for instance, US Patent Application 2004/0243112A1 that was published on Dec. 2, 2004 by M. Bendett et al. entitled "Apparatus and Method for Opthalmologic Surgical Procedures using a Femtosecond Fiber Laser," the contents of which are hereby incorporated by reference. This application describes a method and apparatus for reshaping the cornea without creating a flap that appears to be similar to that described in K. Koenig's Patent Application but with differences such as the proposal to use a fiber fsec laser.

While others appear to appreciate the possible benefits that may result from extending the technique of photodisruption to reshaping the cornea without using a flap they do not appear to have achieved this goal to date. A possible reason is that, to achieve photoablation rather than photodisruption, pulses that are orders of magnitude higher in intensity are required. When such levels of intensity are used, it becomes important to avoid "collateral" damage to the cornea and other eye structures. Furthermore, it becomes necessary to remove large amounts of ablated tissue from the cornea. Neither of the patent applications mentioned above, i.e., neither the 2004/012765 nor the 2004/0243112 application appear to teach how to deliver sufficient laser beam intensity to achieve stroma photo-ablation without damaging other components of the cornea. Moreover, there is no indication given as to how the ablated material could be removed. These are two of the problems that need to be solved before reshaping the cornea without creating a flap becomes practically possible. The requirements for creating a flap with fsec laser pulses through photodisruption of the eye tissue in terms of laser beam intensity, energy and focusing, are, typically, very different than for using photoablation to reshape the cornea. Photoablation of the tissue takes place at laser beam intensities that are typically about two orders of magnitude higher than those used in the process of photodisruption. In photoablation, a relatively large amount of photoablated material needs to be removed from the region of ablation.

In contrast, the present invention relates to a method and apparatus that uses a fsec laser for cornea reshaping without having to cut a flap that resolves, amongst others, these two problems of how to effectively ablate eye tissue without damaging the corneal surface, and how to remove the large amounts of ablated material from within the cornea with cutting a flap.

The present invention takes advantage of the above-described features of ultrashort (preferably fsec, but could be psec) laser pulses for photoablation of eye tissue, in general, and precise photoablation of stroma in the cornea, in particular, without creating a flap.

A first step in our invention is to first "drill" a very small micro channel in the stroma of the eye cornea by directing a fsec laser beam nearly parallel to the surface of the eye that is, nearly perpendicular, or normal, to the axis of the eye. The preferable diameter of the channel is about 50-100 µm, although it can be as large as 200-250 µm). This channel will heal spontaneously after surgery is completed—typically in as little as a few minutes—and is meant primarily to provide access to particular spots within the stroma for photoablation. The length of the channel typically increases during the process of fsec laser "drilling" and may reach 10 mm or more depending on what is required. The fsec laser beam is guided through the channel until it reaches the stroma between the inner (endothelial) and outer (superficial) cornea where it then photoablates a small region (spot) of the stroma. By changing the position of the focusing lens or focusing mirror, the location of the ablation spot moves along the channel. Controlling the number of laser pulses for each spot controls the amount of ablated material in each spot. By changing the angle of the laser beam, which may be accomplished by, for instance, changing the angle of the beam-directing mirror or focusing mirror or both, a new channel at a different location in the stroma may be produced, and additional ablation spots may be formed. By smoothly changing the position of the laser beam by scanning one or both mirrors, the stroma may be ablated in the form of, for example, a disc. The thickness, shape, and vertical profile of the disc can be adjusted by varying the number and sequences of laser pulses at various stroma locations using, for instance, a computer controlled laser pulsing system. The channels created for the fsec laser beam propagation in the cornea (stroma) may also used to permit outflow of the ablated stroma material in the form of gas and liquid. Each channel "self-heals" quickly (typically in minutes) once the laser operation has stopped. Subsequent to the process of photo-ablation of the stroma and the outflow of ablated materials through the laser created channels, the top layer of the cornea collapses and closes the gap between the superficial and endothelial layers of cornea. As a result, the shape of the cornea changes in a form that is controlled by the amount and shape of the volume of ablated material. The process of healing and restoring vision is quick (typically taking no longer than several minutes) and is typically virtually painless since the surface epithelial layer is not violated.

Another objective of the present invention is to describe a method and an apparatus that uses ultrashort (fsec and psec) laser pulses for eye cornea reshaping by means of photo-ablation of stroma using N ultrashort laser beams, where preferably N=2, but could be N=1, or N>2. For example, using two ultrashort pulse beams allows the formation of one channel in the stroma to provide a path for laser photoablation and a second channel (that could lie at some angle to the first channel) that provides a path for removal (self-removal) of gaseous and liquid ablated tissue. In addition, using more than one channel may enable a more precise ablation process. To produce N beams, the laser beam may be split using laser beam optical splitters. For N=2, only one optical splitter is needed, and for N>2, additional optical splitters would be needed.

Another objective of the present invention is to describe a method and an apparatus for the removal of the gaseous and liquid products of tissue photoablation in the stroma of the cornea. The amount and rate of removal of photoablation products should be controlled so as to keep the pressure in the cornea constant. This can be achieved either by adjusting the diameter of the micro-channel used for tissue ablation, or by creating a second channel with the fsec laser solely for the removal of ablated tissue.

A preferred embodiment of the invention will now be described in detail by reference to the accompanying drawings in which, as far as possible, like elements are designated by like numbers.

Although every reasonable attempt is made in the accompanying drawings to represent the various elements of the embodiments in relative scale, it is not always possible to do so with the limitations of two-dimensional paper. Accordingly, in order to properly represent the relationships of various features among each other in the depicted embodiments and to properly demonstrate the invention in a reasonably simplified fashion, it is necessary at times to deviate from absolute scale in the attached drawings. However, one of ordinary skill in the art would fully appreciate and acknowledge any such scale deviations as not limiting the enablement of the disclosed embodiments.

The present invention describes the method and apparatus for correction of vision by means of photoablation of the stroma bed of the eye cornea using ultrashort laser pulses (preferably below 500 fsec, but pulses in the psec range could also be used) without creating a flap. In this invention, a single fsec laser beam is used (that is, N=1), but it teaches how multiple beams (N=2 and N>2) can also be used.

For a single fsec laser beam (N=1), only one channel is created at any one time. This channel is used for laser beam propagation to the stroma, photoablation of the stroma tissue, and the removal of ablated tissue (as a gas and a liquid). The removal of the ablation products is a "self-removal" in that it occurs as a consequence of the pressure generated in the cornea as a result of the ablation process.

Figure 6:
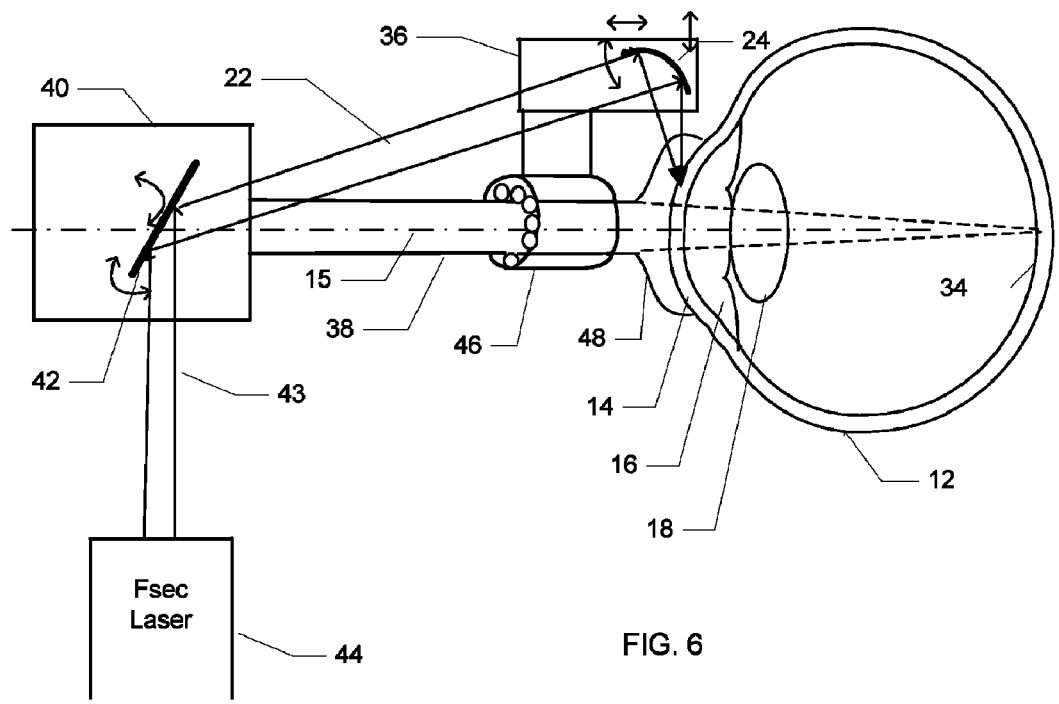
FIG. 6 is a schematic representation of the setup for controlled photoablation of the stroma in the eye cornea using a single (N=1) femtosecond laser beam whereby a computer adjusts and monitors the positions of the beam directing mirror and the focusing mirror.
Figure 9:
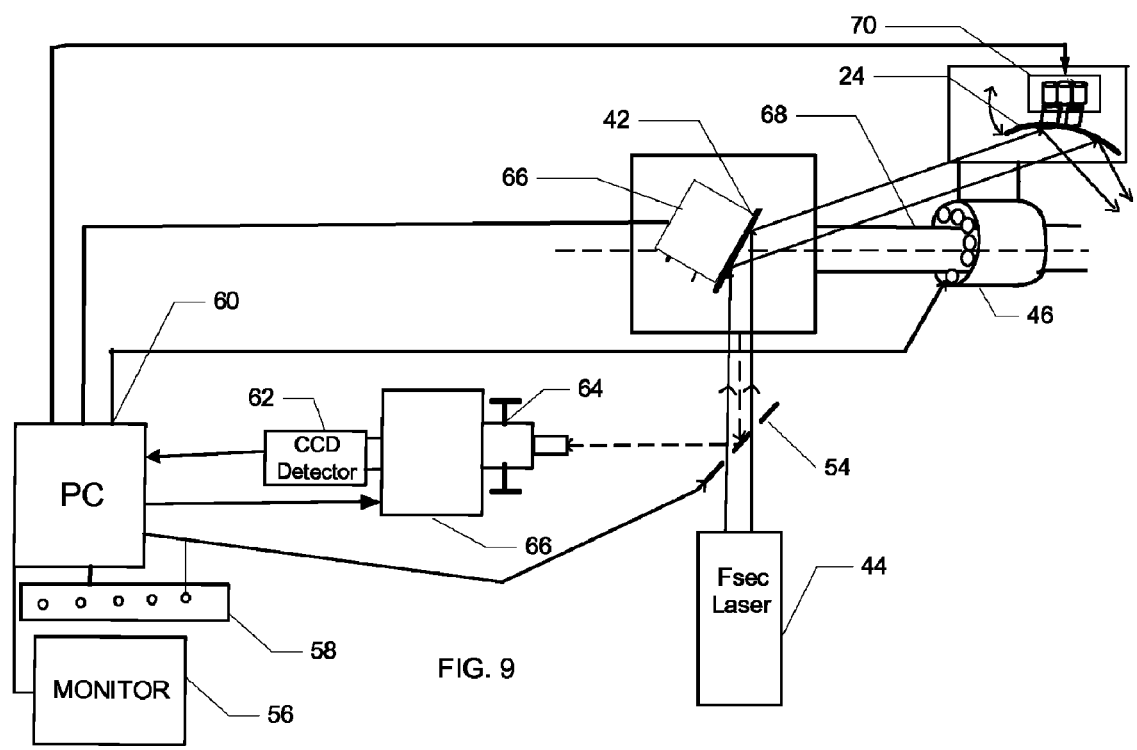
FIG. 9 is a schematic representation of the apparatus used to control the laser beam direction and its focal position in the cornea (stroma).

The channel diameter is preferably 50-100 µm, but could be larger (for example, 200-250 µm is also acceptable). The channel may be several millimeters long (10 mm or more) to allow the laser beam to reach any point in the stroma. In the preferred embodiment, the 500 fsec or shorter laser beam delivers 0.5-1 mJ energy per pulse and the laser repetition rate is 1 kHz or higher (lower repetition rates are also acceptable). The laser beam is directed to the stroma bed by a system consisting of two small mirrors (lenses could also be used). Each mirror is moved and rotated by a system of micro-positioning devices. In the preferred embodiment, for each mirror, two such devices are used for horizontal and vertical movement and three such devices are used for rotational movement, as illustrated in FIGS. 6 and 9. The micro-positioning devices are computer controlled. A computer program controls and monitors the positions of the mirrors and the number of pulses delivered to a pre-determined area of the stroma. The first mirror 42 directs the laser beam to the second mirror 24. In the preferred embodiment, the second mirror is either spherical or off-axis parabolic with a diameter in order of 10 mm. This mirror is located in close proximity to the eye. It directs the laser beam to the stroma bed and it focuses the laser beam on the desired region within the stroma by moving closer to or farther from the eye as well as being rotated.

Figure 7:
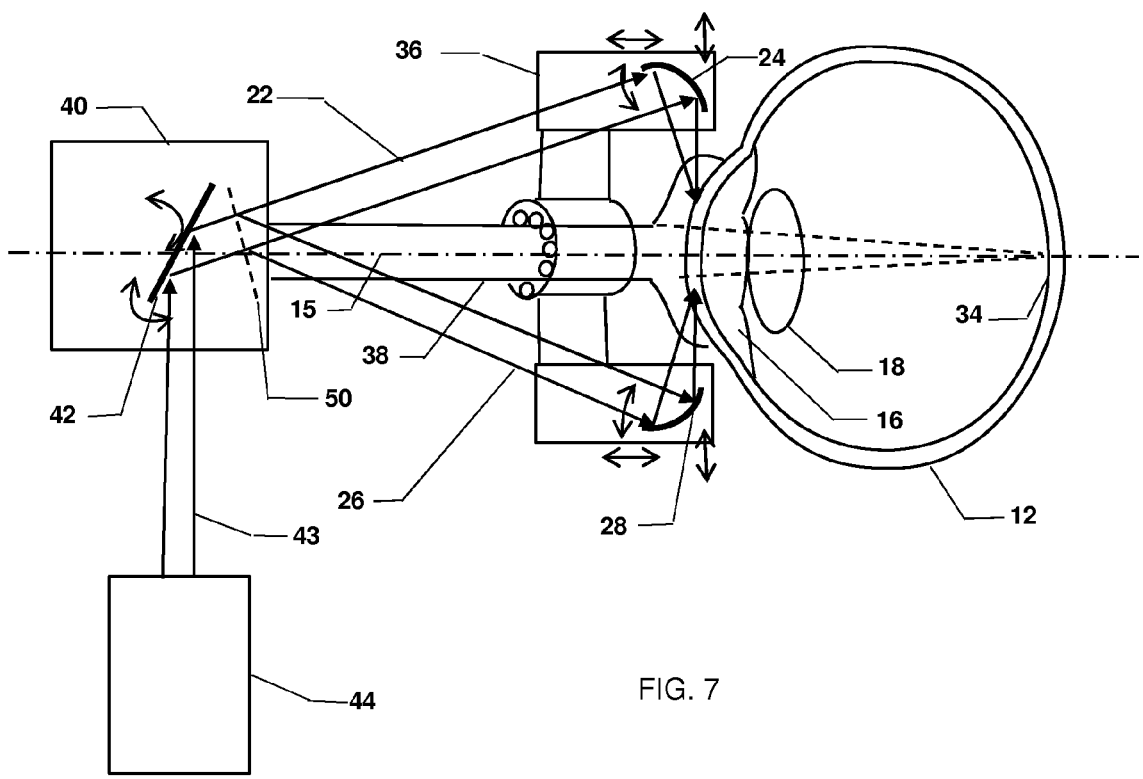
FIG. 7 is a schematic representation of the setup for controlled photoablation of the stroma in the eye cornea, as in FIG. 6, but with two (N=2) fsec laser beams.
Figure 10:
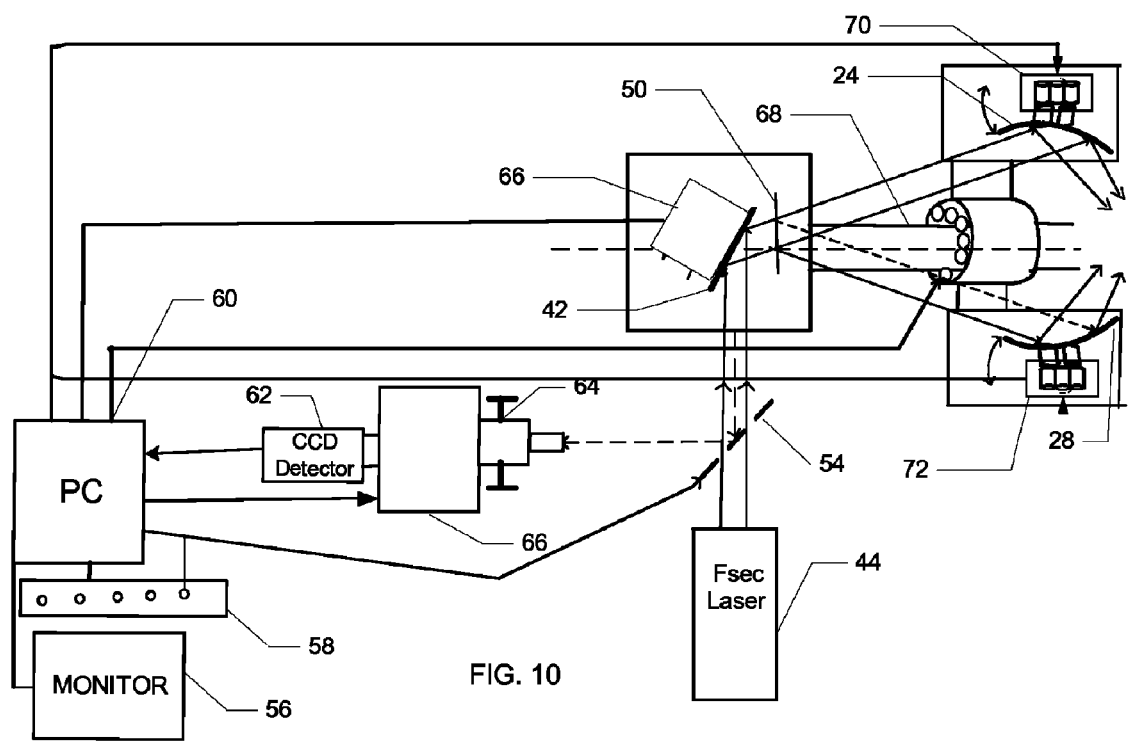
FIG. 10 is a schematic representation of the apparatus used in the process of photoablation of the stroma, as in FIG. 9, but with two (N=2) laser beams.

For N=2 fsec laser beams, the primary fsec laser beam is split into two beams with an optical splitter, as illustrated in FIG. 7, to create two fsec laser beams with approximately equal energy per pulse. The fsec laser is the same as for the N=1 case (described above) but operated preferably with about twice the energy per pulse, that is, 1-2 mJ per pulse. FIG. 10 illustrates the setup for such N=2 case. Here, two small spherical mirrors each focus one beam from approximately opposite sides of the eye. FIG. 3c illustrates the setup where a single spherical (or off-axis parabolic) mirror directs and focuses the two laser beams so that they originate from the same side of the eye in directions that are almost but not quite parallel. This is achieved by directing the two laser beams onto two flat mirrors so that each beam reaches the spherical (or off-axis parabola) mirror, 24, 28, at a slightly different angle.

FIG. 1 is a schematic representation of an ultrashort laser beam 22 focused at a point in a region being ablated 23 in the stroma bed of the cornea 14 of the patient's eye 12. The ultrashort laser beam 22 is directed to the stroma and focused at stroma by the focusing mirror 24. The mirror is preferably spherical or off-axis parabolic, although a lens could be used instead. Also shown in FIG. 1 is the eye lens 18 and the aqueous humor 16.

Figure 2:
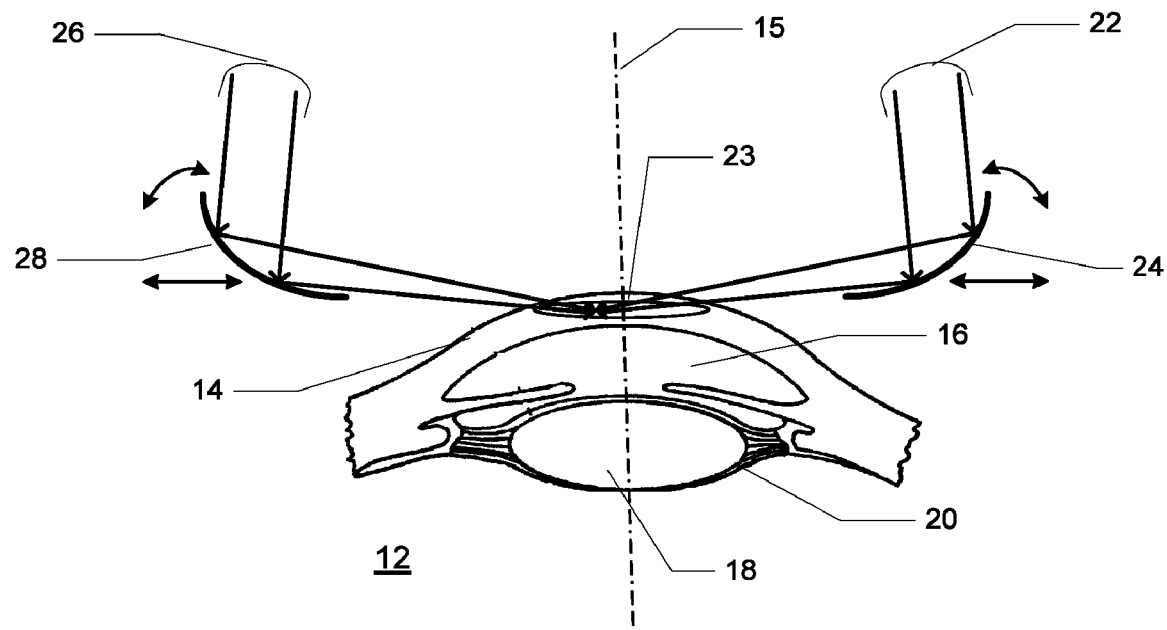
FIG. 2 is a schematic representation of two ultrashort laser beams cross-focused at a point in the stroma of the cornea of the patient's eye.

FIG. 2 is a schematic representation of two ultrashort laser beams, an ultrashort laser beam 22 and second ultrashort laser beam 26, cross-focused at a point in a region being ablated 23 in the stroma of the cornea 14 of the patient's eye 12. The beams are directed to the stroma from approximately opposite sides of the eye's optical axis 15 and are focused at approximately the same spot in the stroma bed by two focusing mirrors, focusing mirror 24 and second focusing mirror 28. The mirrors 26 and 28 are preferably spherical or off-axis parabolic mirrors, although lenses and holographic elements could be used instead.

Figure 3:
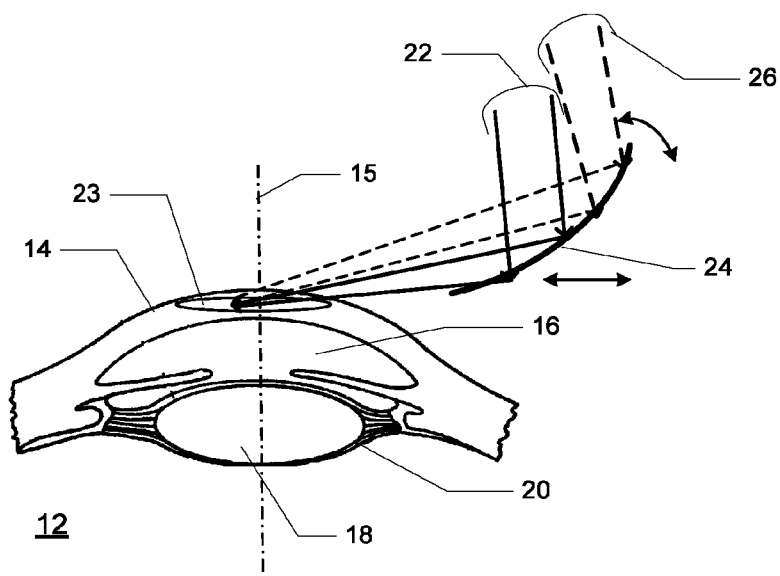
FIG. 3 is a schematic representation of two ultrashort laser beams cross-focused at a point in the stroma bed of cornea of the patient's eye, as in FIG. 2, but here the laser beams are directed to the stroma from the same side of the eye.

FIG. 3 is a schematic representation of two ultrashort laser beams, ultrashort laser beam 22 and a second ultrashort laser beam 26, cross-focused at a point in a region being ablated 23 in the stroma bed of cornea 14 of the patient's eye 14. In contrast to the arrangement of FIG. 2, the two laser beams are directed to the stroma from the same side of the eye. The two laser beams, ultrashort laser beam 22 and second ultrashort laser beam 26, are directed to the region being ablated 23 by two different parts of a single focusing mirror focusing mirror 24, which may, for instance, focus the two beams to approximately the same spot in the stroma.

Figure 4:
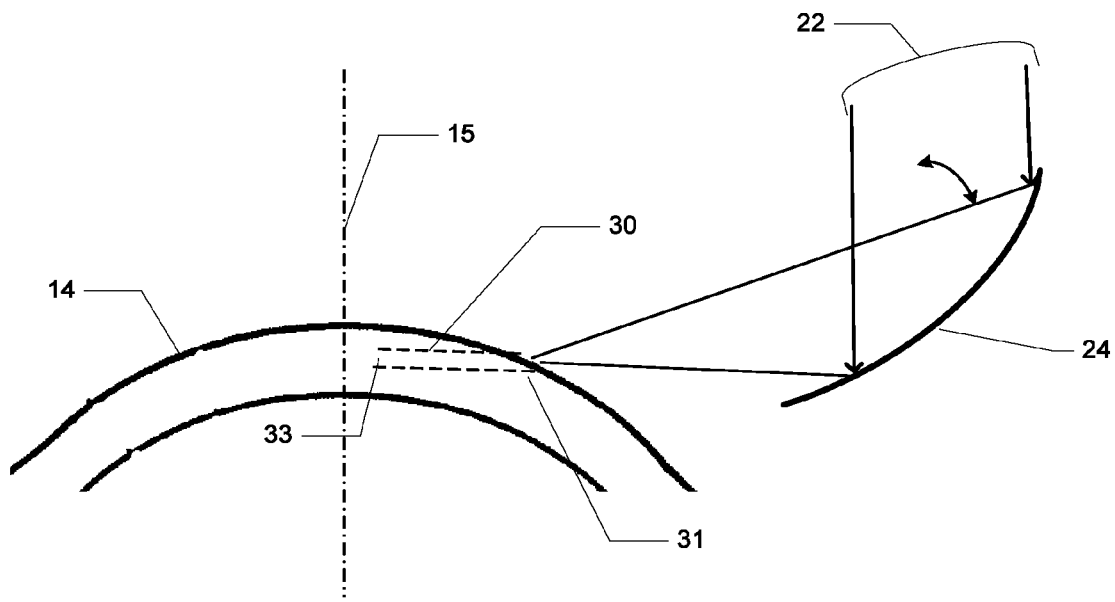
FIG. 4 is a schematic cross-section of creating a micro-channel.

FIG. 4 is a schematic cross-section of creating a temporary micro-channel 30. The ultrashort laser beam 22 is directed by the focusing mirror 24 to a point 31 on the surface of the cornea 14. By delivering a series of ultrashort laser pulses at the appropriate energy and temporal duration, a temporary micro-channel 30 is created by a photodisruption or photoablation or a combination thereof. The temporary micro-channel 30 extends into the cornea 14 to a micro-channel end point 33. The micro-channel end point 33 is typically located within the cornea 14. The temporary micro-channel 30 is substantially normal to the eye's optical axis 15.

Figure 5:
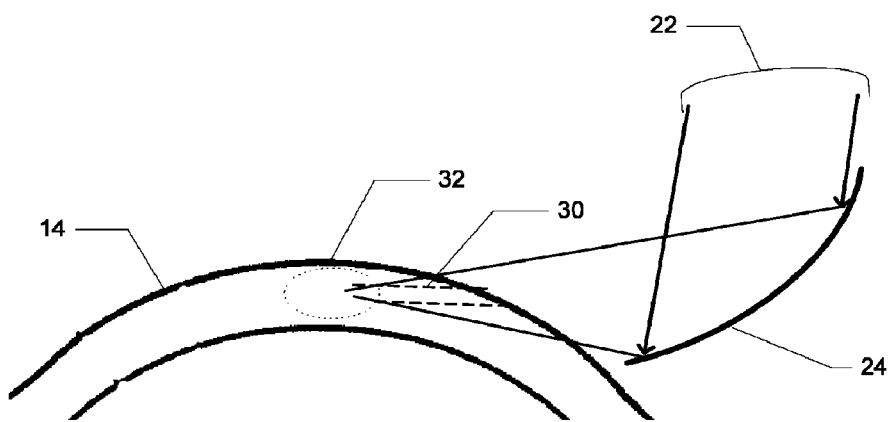
FIG. 5 is a schematic cross-section of ablating a region in the vicinity of the micro-channel end point.

FIG. 5 is a schematic cross-section of ablating a region 32 in the vicinity of the micro-channel end point 33. The ultrashort laser beam 22 delivers a series of ultrashort laser pulses via the focusing mirror 24 and the temporary micro-channel 30 to the micro-channel end point 33. The ultrashort laser pulses are sufficient in number and have a suitable intensity to ablate the cornea 14 in the region 32. The ablated material may exit the region 32 via the temporary micro-channel 30.

FIG. 6 is a schematic representation of the setup for controlled photoablation of the stroma in the eye cornea 14 using a single (N=1) femtosecond laser beam whereby a computer adjusts and monitors the positions of the beam directing mirror and the focusing mirror.

FIG. 7 is a schematic representation of the setup for controlled photoablation of the stroma in the eye cornea, as in FIG. 6, but with two (N=2) fsec laser beams. The primary fsec laser beam 43, after being reflected by the mirror 42, is split by the optical splitter into two laser beams, ultrashort laser beam 22 and second ultrashort laser beam 26. These two laser beams are cross-focused at a point in the stroma bed and directed to the cornea 14 from nearly opposite sides of the eye's optical axis 15 using the focusing mirror 24 and the second focusing mirror 28.

FIG. 6 and FIG. 7 show the instrument employed in reshaping the stroma bed in corrective surgery of the human eye cornea using an ultrashort (fsec- or psec-type) pulsed laser. The primary fsec laser beam 43 from "Fsec Laser" is directed by the mirror 42 to a focusing mirror 24, that may be a spherical mirror, which focuses the laser beam at different locations within the cornea 14. The mirror 42 and focusing mirror 24 may be placed on two separate platforms that are mechanically connected to a cylinder 38. The first platform 40, on which the mirror 42 is mounted, may be rigidly connected to the cylinder 38. Cylinder 38 may provide a stabilization mechanism 48 for the eye 12. The second platform 36, on which the focusing mirror 24 is located, may rotate around cylinder 38 by means of a rotating mechanism 46. Rotation of the second platform 36 may, for instance, be synchronized with the angular movement of mirror 42 in such a way that the ultrashort laser beam 22 reflected by mirror 42 always passes onto focusing mirror 24. Micro-positioning devices that are controlled and monitored by a computer set the angle of the mirror 42. The angle and position of focusing mirror 24 on the second platform are also set by micro-positioning devices that are controlled and monitored by the same computer. In this way, the "Fsec Laser" beam can be focused by the mirror MS into any part of the cornea.

The procedure in a preferred embodiment uses a laser with pulses of 500 fsec in duration and shorter, operating at a wavelength near 800 nm, at repetition rates at least 1 kHz and preferably significantly higher, and with an energy per pulse in the range of 0.1-1.0 mJ, but lower or higher energies are acceptable as well. This range of energy per pulse can be decrease down to the range of 10-50 micro-Joules when using fsec laser with pulse duration about 10-20 fsec. For such short pulse duration preferably repetition rates is 10 kHz and higher.

For cornea ablation the wavelength of the laser is not of prime importance because for ultrashort laser pulses the dominant process leading to ablation of the eye material (in this case the stroma in the cornea) is based on a multiphoton process, in contrast to the process that uses much longer laser pulses (produced by nanosecond-type lasers) where ablation is dominated by atoms, electrons, and ions, which are heated by laser pulses.

In order to photoablate some particular volume of the cornea tissue, for example, a "disc" 2 mm in diameter and 50 micrometers thick located 150-200 micrometers below the surface of the eye, the focusing mirror 24 would focus the laser beam initially on the central part of the stroma. The action of the laser beam will first create a "micro-channel" of a very small diameter (preferably 50-100 micrometers in diameter, although it can be 200-250 micrometers as well), and several millimeters long, covering the distance between surface of the eye and the desired ablation point within the cornea. Once the channel is created, the laser beam is passed through the channel and focused at the desired location to start ablating the stroma. The same micro-channel (or an additional one) provides a means of self-removal of the ablated stroma tissue in the form of gas and liquid under the over-pressure created within the ablated volume in the process of photoablation. Such small channels will usually close without further intervention in a matter of minutes after the process of photoablation is completed.

By rotating the second platform around cylinder 38, changing the position of focusing mirror 24 on the platform, and by changing its direction (angle), the ultrashort laser beam 22 may be used to ablate a disc of corneal tissue of any reasonable, required dimension. The thickness and shape of such a disc may be determined by, for instance, controlling the number of laser shots delivered to any given point within the disc. The ablation process is monitored in terms of location and uniformity by using an optical microscope through standard techniques such as those presently applied in laser eye surgery and described in more detail in the patents incorporated by reference above. If necessary, additional channels may be formed in the stroma of the cornea using the same fsec laser in order to increase the rate of removal of the gases and liquids produced as part of the photoablation process.

FIG. 9 shows in more detail how the laser beam direction and focus position in the cornea are set using mirrors ML and MS. The position of the laser beam within the cornea, and the process of photoablation, is monitored through a microscope outfitted with a CCD detector, and the signal is directed to the computer and a monitor.

The procedure in a preferred embodiment uses a laser with pulses of 500 fsec in duration and shorter, operating at a wavelength near 800 nm, at repetition rates at least 1 kHz and preferably significantly higher, and with an energy per pulse in the range of 0.1-1.0 mJ, but lower or higher energies are acceptable as well. This range of energy per pulse can be decrease down to the range of 10-50 micro-Joules when using fsec laser with pulse duration about 10-20 fsec. For such short pulse duration preferably repetition rates is 10 kHz and higher.

For cornea ablation the wavelength of the laser is not of prime importance because for ultrashort laser pulses the dominant process leading to ablation of the eye material (in this case the stroma in the cornea) is based on a multiphoton process, in contrast to the process that uses much longer laser pulses (produced by nanosecond-type lasers) where ablation is dominated by atoms, electrons, and ions, which are heated by laser pulses.

In order to photoablate some particular volume of the cornea tissue, for example, a "disc" 2 mm in diameter and 50 micrometers thick located 150-200 micrometers below the surface of the eye, the mirror MS would focus the laser beam initially on the central part of the stroma. The action of the laser beam will first create a "micro-channel" of a very small diameter (preferably 50-100 micrometers in diameter, although it can be 200-250 micrometers as well), and several millimeters long, covering the distance between surface of the eye and the desired ablation point within the cornea. Once the channel is created, the laser beam is passed through the channel and focused at the desired location to start ablating the stroma. The same micro-channel (or an additional one) provides a means of self-removal of the ablated stroma tissue in the form of gas and liquid under the over-pressure created within the ablated volume in the process of photoablation. Such small channels will usually close without further intervention in a matter of minutes after the process of photoablation is completed.

By rotating the second platform 36 around cylinder 38, changing the position of focusing mirror 24 on the platform, and by changing its direction (angle), the ultrashort laser beam 22 may be used to ablate a disc of corneal tissue of any reasonable required dimension. The thickness and shape of such a disc, may for instance, be determined by controlling the number of laser shots delivered to any given point within the disc. The ablation process may be monitored in terms of location and uniformity by using an optical microscope through standard techniques such as those presently applied in laser eye surgery. If necessary, additional channels may be formed in the stroma of the cornea using the same fsec laser in order to increase the rate of removal of the gases and liquids produced as part of the photoablation process.

Figure 8:
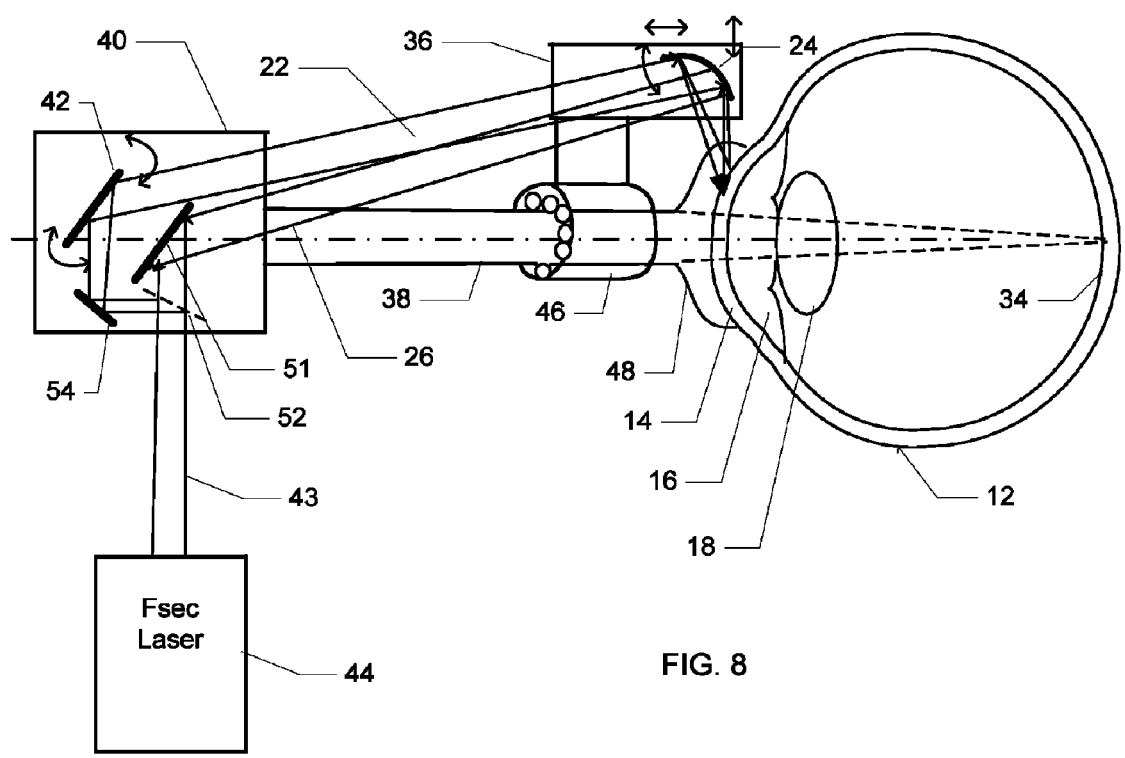
FIG. 8 is a schematic representation of the setup for controlled photoablation of stroma bed in eye cornea, as in FIG. 7, but with two fsec laser beams cross-focused at a point in stroma bed under some angle (preferably small angle).

FIG. 8 is a schematic representation of the setup for controlled photoablation of stroma bed in eye cornea, as in FIG. 7, but with fsec laser beams cross-focused at a point in stroma bed under some angle (preferably small angle). The primary fsec laser beam 43, before reaching directional mirror 51, is divided into two laser beams by optical splitter 52. The second ultrashort laser beam 26 has a similar path as ultrashort laser beam 22 in FIG. 6, whereas the first ultrashort laser beam, after reflection from mirror 54 and another directional mirror 42, is focused on or near the same point of the stroma as ultrashort laser beam 22 using the same focusing mirror 24.

FIG. 9 is a schematic representation of the apparatus used to control the laser beam direction and its focal position in the cornea (stroma). The directional mirror 42 is preferably flat, and the focusing mirror 24 is preferably spherical or off-axis parabolic although it could also be a lens. The directional and focusing mirrors are each controlled by a system of micro-positioning devices 70, that may for instance be five micro-positioning devices for vertical, horizontal, and three rotational positions). A computer 60 controls the micro-positioning devices 70. The location of the laser beam within the cornea (as is shown in FIG. 2a), and the process of photoablation, is monitored by the computer 60 through an optical microscope 64 fitted with a CCD detector 62. Laser light reflected from the cornea (a very small fraction of its initial energy) is directed to the microscope by a low reflectance mirror 54 (transmitting preferably more than 98% of ultrashort laser beam energy on its path towards directional mirror and reflects towards the optical microscope 64 the light reflected from the cornea and the eye).

FIG. 10 is a schematic representation of the apparatus used in the process of photoablation of the stroma, as in FIG. 9, but with two (N=2) laser beams. The optical splitter 50, located just after the directional mirror 42, divides the laser beam into two beams of approximately equal energy. The two beams are directed to the cornea from approximately opposite sides of eye axis, as shown in FIG. 2b. Two focusing mirrors, focusing mirror 24 and second focusing mirror 28 that are either spherical or off-axis parabolic control the directions and focal positions of the two laser beams in the cornea. The vertical, horizontal, and three rotational positions of the focusing mirror 24 and the second focusing mirror 28 are determined by a system of micro-positioning devices 70 and 72 controlled by a computer 60. A similar system of micro-positioning devices 66 controlled by the computer 60 is used to control the position of the directional mirror 42.

Figure 11:
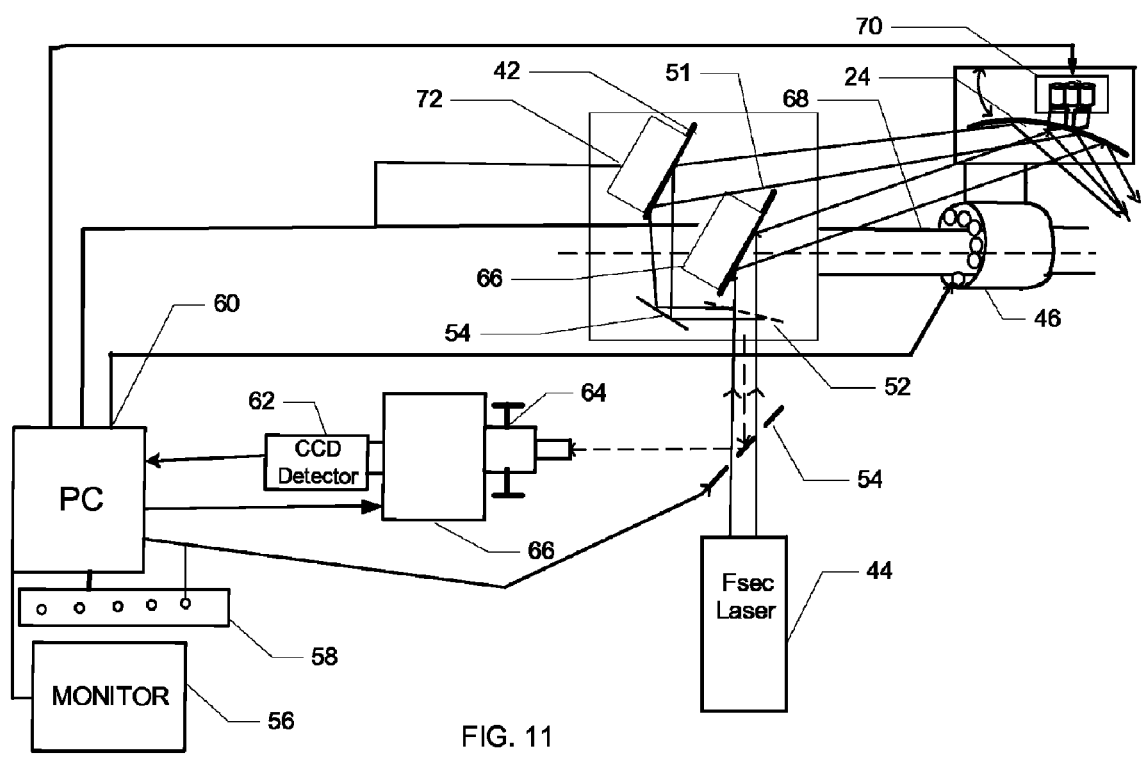
FIG. 11 is a schematic representation of the apparatus used in the process of photoablation of the stroma bed, as in FIG. 10, but with two laser beams directed to the cornea from the same side of the eye axis with a small angle between them, as shown in FIG. 2c.

FIG. 11 is a schematic representation of the apparatus used in the process of photoablation of the stroma bed, as in FIG. 10, but with two laser beams directed to the cornea from the same side of the eye axis with a small angle between them, as shown in FIG. 2c. The optical splitter 52, located just in front of the directional mirror 51, divides the laser beam into two beams of approximately equal energy. One beam proceeds to the mirror 51, while the second beam, after being reflected by mirror 54, is directed to mirror 42. The beams from mirrors 42 and 51 are directed toward the focusing mirror 24. Mirror 24 directs the beams to approximately the same spot in the stroma, but each beam comes to and is reflected from different parts of mirror 24. The mirrors 42, 51, and 24 are individually controlled by separate systems of micro-positioning devices via a computer 60, as in FIGS. 9 and 10.

The layout of two other preferred embodiments of the invention are presented in FIGS. 7, 10, 8, and 11, which are similar to the embodiment presented in FIGS. 6 and 9, but instead use N=2 fsec laser beams, obtained by splitting the primary fsec laser beam into two beams by means of an optical splitter 52. In a preferred embodiment presented in FIGS. 7 and 10, the two beams are directed to essentially opposite sides of the cornea and focused on approximately the same spot of the stroma with focusing mirrors 24 and 28. In a preferred embodiment presented in FIGS. 8 and 11, the two beams are directed to essentially the same side of the cornea (at a small angle to each other) and focused on approximately the same spot of the stroma bed using one focusing mirror 24. Other arrangements, using lenses instead of mirrors, and N>2 laser beams, are also possible. Applying two laser beams simultaneously as presented schematically in FIGS. 7 and 10 and FIGS. 8 and 11, may be more advantageous than applying a single laser beam as presented in FIGS. 6 and 9, because one beam can be used to create the micro-channel in the cornea for photoablation purposes while the second beam can be used to create a micro-channel for self-removal of the ablation products (ablated corneal tissue). Another possible advantage of applying two laser beams simultaneously is that it may lead to a faster and more precise photoablation process. Using two laser beams for cornea reshaping instead of one, however, may make the preferred embodiments more complicated. All instrumentation, apparatus and procedures in the preferred embodiments shown in FIGS. 7, 10, 8, and 11 may be similar to the embodiments presented in FIGS. 6 and 9.

2. Computer Program and Procedure

Figure 12:
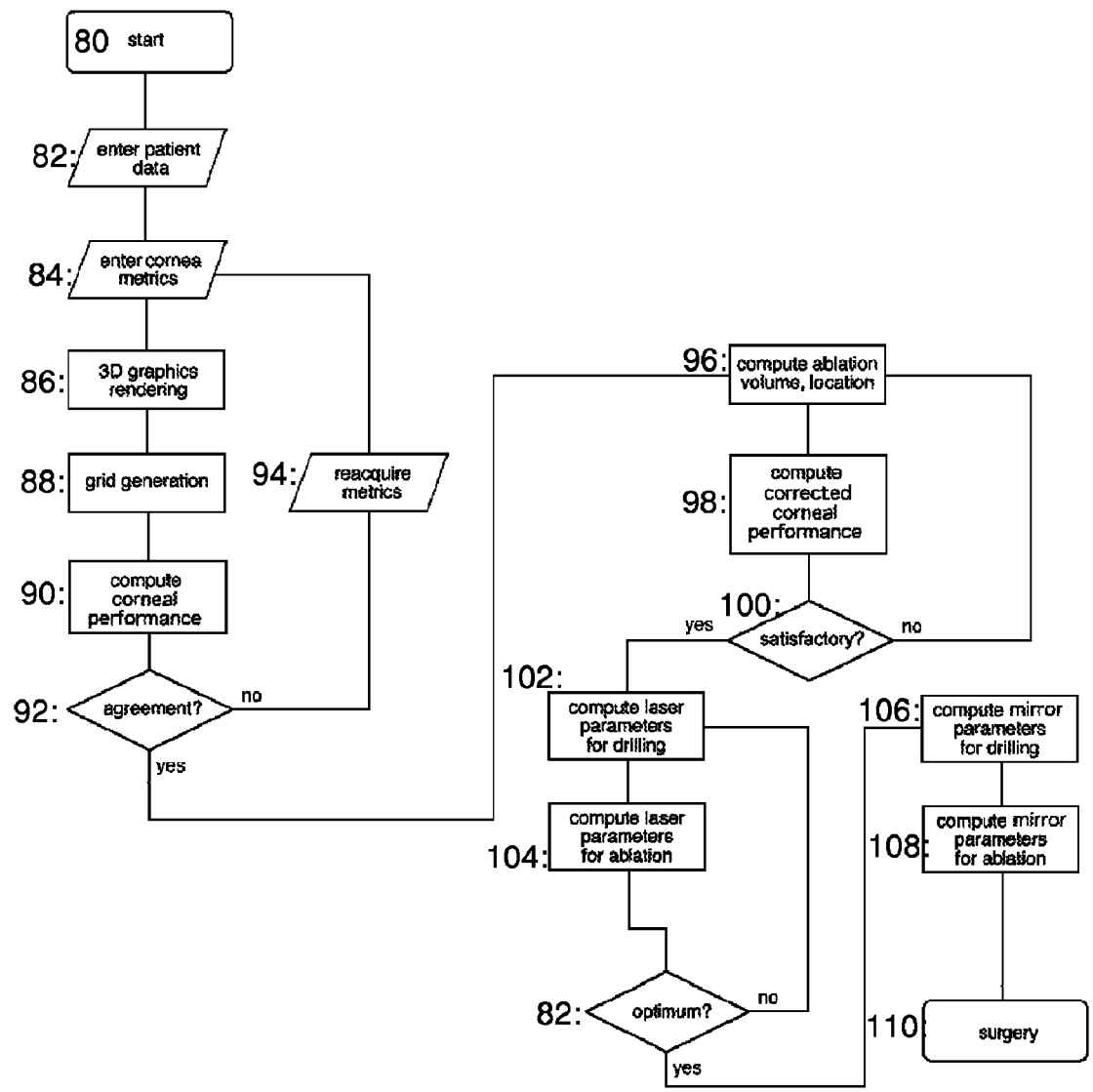
FIG. 12 shows a flow chart describing the computer program that generates laser and mirror parameters for cornea reshaping using an ultrashort pulse laser.

FIG. 12 shows a flow chart describing the computer program that generates laser and mirror parameters for cornea reshaping using an ultrashort pulse laser. The procedure comprises four blocks of steps: (1) computation of corneal refractive power based on patient-specific data; (2) computation of optimum size, shape and location of corneal tissue to be ablated; (3) computation of laser parameters for drilling micro-channels and performing photoablation; and (4) computation of horizontal, vertical, and rotational movement of mirror micro-positioning devices.

The flow chart of FIG. 12 describes a procedure for cornea reshaping of the human eye using a specifically designed algorithm. The software embodied in the steps of this flow chart may provide an instruction set for the laser output and for the mirror, or lens, positioning systems that may be used to perform corrective surgery on the cornea by cornea reshaping without the use of a flap.

The software may proceed in four major blocks of steps.

In a first block that begins with step 80 of starting, patient-specific data on the eye cornea is entered in step 82, and data related to cornea in general are entered in step 84, so that the optical and mechanical performance of the particular cornea may be computed in step 90. In step 82 metrics related to the measured performance of the patient's cornea are entered. In step 84 general data related to cornea in general are entered. In step 86, a 3D model of the patents cornea may be made. This model may be made by, for instance, a commercially available design tool such as, but not limited to, well known design tools such as AutoCAD or ProEngineer. These tools may be used to model the geometry of the cornea. Information not available from the patient is modeled using population norms that may be part of the data entered in step 84. The geometry generated in step 86 may then be imported into a grid generation program in set 88 using, for instance, one of the well known grid generating software packages such as, but not limited to, GRIDGEN. The grid generated in step 88 may then be then exported to a finite-element program for computing the optical power of the cornea in step 90. This computation may be done using patient-specific values of the refractive index, where available. Such software may be generated using well know optical ray trace algorithms and equations. Once the performance of the model cornea is computed in step 90, the output is compared to the power of the cornea as measured in the patient in step 92. If the modeled and the measured performance of cornea are not in agreement, or the agreement is not satisfactory, the corneal metrics may be reacquired, and the computation is started afresh using different assumptions about average values. If the agreement is satisfactory, the software proceeds to the Block 2.

In Block 2, the parameters regarding the volume to be ablated are computed. In step 98 the software computes the size, shape, and location of the volume based on the desired performance of the cornea after correction. An optimization scheme may used to determine the minimum volume that needs to be removed from the cornea and its location. In step 96, a candidate volume may be proposed. This candidate is a starting point for the optimization, and can be a pre-assigned size, shape and location based on previous experience. Multiple ablation volumes may also be considered. The program then proceeds to step 98 to compute the power of the cornea after correction. To determine the optimum surgical option, a cost function may be computed on the basis of, for instance, the minimum ablation volume, the most peripheral position of volume, the fewest delivery channels, and other similar additional constraints. The computation may then be restarted using a small perturbation from the original volume choice, and the cost function may be recomputed. Through this iterative process an optimal surgical strategy may be found. If, in step 100, the parameters are satisfactory, based on the level of corrective surgery required, the presence or absence of corneal defects, the general health of the patient, as well as other relevant medical input, the software may then proceed to Block 3.

In Block 3, the output from Block 2 is used to compute the laser parameters for drilling micro-channels and for photoablation. In step 102, the software used the output from step 100. In step 102, the laser parameters for drilling the temporary micro-channels may be computed. In step 104, the laser parameters for performing the required ablation are calculated. The laser parameters may include power per shot, number of shots, repetition rate, positioning and focusing of laser beam(s), and shot pattern. An optimization scheme may used to determine the minimum number of channels.

In Block 4, the output from Block 3 is used to compute the mirror (or lens) parameters for drilling the required micro-channels and for performing the photoablation. In step 106, the mirror parameters for drilling the required micro-channels are calculated. In step 108 the mirror parameters for performing the required ablation are calculated. For each mirror the parameters may include its horizontal, vertical, and rotational movement. The computer program may also compute the required instructions to each of the micro-positioning devices to obtain the required mirror parameters.

In step 110, the actual surgery is performed. The may be done with the program controlling and monitoring the positions of all the mirrors and the number of pulses delivered to predetermined areas of the stroma bed.

The output from the software suite may consist of specific instructions for the size, shape and location of the ablation volume(s), the laser parameters recommended to achieve the specified ablation volume and channel drilling, including all instructions on the laser parameters (power per shot, number of shots, repetition rate, positioning and focusing of laser beam(s), shot pattern) that may be directly used to program the laser output, and the computer-generated instructions for the mirror positioning systems that can be used directly to program these systems.

Although the invention has been described in language specific to structural features and/or methodological acts, it is to be understood that the invention defined in the appended claims is not necessarily limited to the specific features or acts described. Rather, the specific features and acts are disclosed as exemplary forms of implementing the claimed invention. Modifications may readily be devised by those ordinarily skilled in the art without departing from the spirit or scope of the present invention.

What is claimed is:

1. A method for removing material from an interior portion of a cornea without creating a flap, said method comprising the steps of:
   creating a temporary micro-channel extending from a surface of said cornea to a micro-channel end point located within said cornea by delivering a first plurality of ultra-short laser pulses; and
   multi photon ablating material in a vicinity of said micro-channel end point by delivering a second plurality of ultra-short laser pulses with pulse energies of 20 µJ or greater and focused down to a pulse intensity between a range of $10^{13}$ to $10^{15}$ W/cm$^2$.

2. The method of claim 1 wherein said micro-channel is oriented substantially normal to the optical axis of said cornea.

3. The method of claim 2 wherein said first plurality of ultra-short laser pulses forming said micro-channel are delivered in a first window of time, are directed substantially normal to the optical axis of said cornea, have a pulse duration of 500 femtoseconds or less, have a pulse energy of 5 mJ or less, have a repetition rate of 1 kHz or greater and are focused down to a diameter of between 50 and 100 µm, and wherein said second plurality of ultra-short laser pulses is are delivered in a second window of time.

4. The method of claim 3 wherein each pulse of said second plurality of ultra-short laser pulses is directed substantially normal to said optical axis, and wherein said multi-photon ablating creates an over-pressure within the ablated area of the cornea causing an outflow of said ablated material in the form of a gas or liquid via said micro-channel.

* * * * *